United States Patent [19]

Ishibe et al.

[11] 4,368,338
[45] Jan. 11, 1983

[54] DEGREASER SOLVENT STABILIZATION

[75] Inventors: Nobuyuki Ishibe; Jimmie K. Harden nee Ashley, both of Lake Jackson, Tex.

[73] Assignee: The Dow Chemical Company, Midland, Mich.

[21] Appl. No.: 274,893

[22] Filed: Jun. 18, 1981

[51] Int. Cl.$^3$ .................. C07C 21/10; C07C 21/12
[52] U.S. Cl. .................. 570/109; 252/364; 570/112; 570/117
[58] Field of Search .............. 252/364; 570/109, 112, 570/117

[56] References Cited

U.S. PATENT DOCUMENTS

| | | | |
|---|---|---|---|
| 2,492,048 | 12/1949 | Klabunde | 570/109 |
| 2,721,883 | 10/1955 | Stevens | 570/109 |
| 2,795,623 | 6/1957 | Starks | 570/117 |
| 2,887,516 | 5/1959 | Ferri et al. | 570/117 |
| 3,040,108 | 6/1962 | Campbell | 570/109 |
| 3,230,175 | 1/1966 | Martens | 570/109 |
| 3,269,953 | 8/1966 | Boothman | 570/109 |
| 3,314,892 | 4/1967 | Graham | 570/109 |
| 3,397,246 | 8/1968 | Ryckaert et al. | 570/109 |
| 3,798,170 | 3/1974 | Petering et al. | 570/109 |
| 3,845,147 | 10/1974 | Richtzenhain et al. | 570/112 |
| 3,862,250 | 1/1975 | Beckers | 570/112 |

FOREIGN PATENT DOCUMENTS

| | | | |
|---|---|---|---|
| 47-10683 | 3/1972 | Japan | 570/112 |
| 430671 | 8/1967 | Switzerland | 570/109 |

*Primary Examiner*—Allan Lieberman
*Attorney, Agent, or Firm*—A. C. Ancona

[57] ABSTRACT

A stabilized chlorinated solvent composition useful in removing grease from metals wherein the solvent is perchloroethylene or trichloroethylene, and the stabilizer is N-methyl pyrrole in combination with ethyl acetate, acetonitrile or pyrazine.

6 Claims, No Drawings

DEGREASER SOLVENT STABILIZATION

BACKGROUND OF THE INVENTION

The removal of grease films from metal surfaces by the application of grease solvents has been widely practiced during recent years. Numerous solvents have been employed, and numerous variations of the degreasing procedure have been suggested. In one method of operating, the metal article to be degreased is brought into contact with the solvent in the liquid phase. This may be accomplished by immersing the article in a large body of the solvent, or by spraying the solvent on the surface of the article. In another common method of degreasing, known generally as vapor-phase degreasing, a body of solvent is maintained at the boiling point and in communication with a chamber adapted to contain a large body of the solvent vapor. The article to be degreased is brought into contact with this body of vapor, and causes condensation of the solvent on the greasy metal surface. The condensed solvent removes grease and oil from the metal surface and drips off, usually returning to the boiling body of the solvent. With it goes dirt, adhering to the greasy surface. This dirt often includes metal chips.

Numerous solvents have been employed in degreasing operations. Among these, solvents of the chlorinated hydrocarbon type, including both saturated compounds such as carbon tetrachloride, and unsaturated compounds such as trichloroethylene and perchloroethylene, have been widely employed because of their high grease-solvent capacity and low flammability. Trichloroethylene is probably most widely used in degreasing. However, it is seldom used without the addition of some "stabilizer," adapted to prevent or retard its decomposition during storage and normal use. This so-called "normal" type of decomposition is promoted by light and oxygen. The action of light and oxygen is accelerated by heat. Several stabilizers are available and commonly used for the purpose of inhibiting this decomposition.

Pyrrole and N-alkyl pyrroles, especially those in which the alkyl group contains 1 to 4 carbon atoms, are the preferred stabilizers for this purpose. Examples of these are pyrrole, N-methyl pyrrole, N-ethyl pyrrole, 2-methyl pyrrole, 3-methyl pyrrole, 2,4-dimethyl pyrrole, 2,5-dimethyl pyrrole, N-propyl pyrrole and 2-chloropyrrole. The use of these stabilizers was first disclosed in U.S. Pat. No. 2,492,048. Another well-known inhibitor or stabilizer for trichloroethylene or perchloroethylene when used as a degreasing solvent is a group of organic esters. These are esters formed by the reaction of an aliphatic alcohol with an aliphatic carboxylic acid, each of which alcohol and acid can contain up to six carbon atoms. Specific examples include ethyl acetate, isopropyl acetate, butyl hexanoate, amyl acetate, n-butyl formate and the like. The above are disclosed as useful for stabilizers in U.S. Pat. No. 2,371,647.

A combination stabilizer is disclosed in U.S. Pat. No. 2,818,446 wherein esters such as the above are combined with an epoxide such as propylene oxide, butylene oxide or epichlorohydrin. Ethyl acetate and epichlorohydrin is a preferred combination.

Epoxides are also used in combination with amines as disclosed in U.S. Pat. No. 2,797,250. Amines both aliphatic, such as triethylamine, and aromatic, such as pyridine and the picolines, are useful in combination with epoxides such as butylene oxide or epichlorohydrin.

Another combination stabilizer, described in U.S. Pat. No. 2,906,783, consists of an epoxide, an ester, an alkene hydrocarbon and an azine. For example, trichloroethylene was stabilized by the addition of butylene oxide, isopropyl acetate, trimethylpentene and acetalazine. Other useful azines are derivatives of aliphatic aldehydes, e.g. propionaldehyde azine or butyraldehyde azine. Pyrazine and nitriles have been used to stabilize methylchloroform as disclosed in U.S. Pat. No. 3,798,170 and 3,564,063, respectively.

The present invention is a new stabilizer combination in which N-methyl pyrrole is employed with (1) an ester, e.g. ethyl acetate, or (2) a nitrile, e.g. acetonitrile, or (3) pyrazine in trichloroethylene or perchloroethylene when used in degreasing operations.

SUMMARY OF THE INVENTION

The invention of this application is a stabilizer system for trichloroethylene or perchloroethylene when employed in vapor degreasing operations, which is comprised of the particular solvent in combination with N-methyl pyrrole together with an aliphatic ester, or an aliphatic nitrile, or pyrazine.

DETAILED DESCRIPTION OF THE INVENTION

Various tests were made on trichloroethylene containing N-methyl pyrrole which also contained an ester, an aliphatic nitrile or pyrazine. Description of the tests are as follows:

1. Seven-day reflux (steel, aluminum)

Steel wool or Al-2024 chips (1 g) were placed in a 1:1 mixture of the formulated trichloroethylene and water (50 ml), and refluxed under nitrogen for 7 days. After separation from the aqueous layer, the organic layer was analyzed by gas chromatography to quantify the dimer (hexachlorobutene and/or tetrachlorobutadiene).

2. Three-day reflux ($AlCl_3$, Al)

The mixture of a formulated trichloroethylene with Al powder and anhydrous $AlCl_3$ was refluxed for 1–3 days to see if the runaway reaction occurs.

3. Accelerated oxidation (acidity)

A trichloroethylene solution containing 5% water was heated in the presence of an iron coupon and oxygen was bubbled through the solution for 24 hours. The mixture was titrated with an alkali solution to determine the extent of acid formation.

4. Seven-day reflux (various metals)

Unfractionated and fractionated solutions of equal volume were refluxed for 7 days under dry or wet (7% water added) conditions in the presence of metals such as Al-1100, 2024, 7074, Zn, Cu, Ni, steel, stainless steel, brass, and monel. Corrosion of metals and discoloration of solutions were judged visually.

Results of tests 1–3 above are shown in Table I. Some of the stabilizer compositions are shown as a range of the components and the results may also be ranges related inversely to the component concentration.

Results of test 4 above the seven-day reflux test, are shown in Table II.

TABLE I

| Component* (wt.%) | Metals (Dimer) (ppm) Al | SW* | Acidity ppm | % Increase | AlCl₃—Al Reflux |
|---|---|---|---|---|---|
| Blank | 23 | 21 | 161–186 | 1550–1800 | Fail |
| BO (0.2–0.5) | 13–35 | 10–17 | 12.2 | 115 | Pass |
| EA (0.1–0.5) | 0 | 3 | 58.1 | 654 | — |
| AN (0.1–0.5) | — | — | 27.2 | 252 | Pass |
| PY (0.1–0.5) | 1 | 3 | 56–185 | 450–1700 | — |
| NMP (0.02) | | 2 | 10.2 | 2.0 | Fail |
| NMP (0.01–0.02) + EA (0.1–0.5) | 0 | 0 | 9.3 | 2.9 | Pass |
| NMP (0.02) + AN (0.1–0.5) | 0 | 0 | 9.4–12.8 | 4.4–43.2 | Pass |
| NMP (0.01–0.02) + PY (0.25–0.5) | 0 | 0 | 7.6–10.8 | 3.3–5.3 | Pass |

*Abbreviations employed are:
BO = butylene oxide;
EA = ethyl acetate;
AN = actonitrile;
NMP = N—methyl pyrrole
PY = pyrazine
SW = steel wool

TABLE II
SEVEN-DAY REFLUX WITH VARIOUS METALS[a]

| Run[b] | Metal | Unfractionated Dry | Wet[c] | Top Fraction Dry | Wet[c] | Bottom Fraction Dry | Wet[c] |
|---|---|---|---|---|---|---|---|
| 1 | Al-2024 | 3 | 3 | 0–1 | 0–1 | 0–1 | 0–1 |
|   | Al-7075 | 0–1 | 2 | 0–1 | 0–1 | 0–1 | 0–1 |
|   | Zn | 2 | 4 | 0–1 | 0–1 | 0–1 | 0–1 |
|   | Fe | 0–1 | 2 | 0–1 | 0–1 | 0–1 | 0–1 |
|   | SS-304 | 0–1 | 3 | 0–1 | 0–1 | 0–1 | 0–1 |
| 2 | Zn | 0–1 | 0–1 | 2 | 0–1 | 0–1 | 2 |
|   | Fe | 2 | 3 | 3 | 5 | 2 | 3 |
| 5 | Zn | 0–1 | 4 | 0–1 | 0–1 | 0–1 | 2 |
|   | Fe | 0–1 | 3 | 0–1 | 4 | 3 | 3 |
| 7 | Zn | 0–1 | 2 | 0–1 | 2 | 0–1 | 2 |
|   | Fe | 0–1 | 2 | 0–1 | 2 | 2 | 3 |
| 9 | Zn | 0–1 | 0–1 | 0–1 | 2 | 0–1 | 0–1 |
|   | Fe | 0–1 | 2 | 0–1 | 3 | 0–1 | 3 |

[a]Rating zero is the best and five the worst.
[b]The number corresponds to that in Table I.
[c]7% water is added.

The present invention, then, is a combination of stabilizers for the solvents trichloroethylene or perchloroethylene, wherein the stabilizer combination includes from about 0.01 to about 0.5% N-methyl pyrrole together with from about 0.1 to about 1% ethyl acetate, or from about 0.1 to about 1% acetonitrile, or from about 0.1 to about 1% pyrazine based on the total weight of solvent and stabilizer combination.

Preferred combinations, same basis, are 0.02 to 0.05% NMP and 0.2 to 0.5% EA; 0.02 to 0.05% NMP and 0.2 to 0.5% AN and; 0.02 to 0.05% NMP and 0.2 to 0.5% PY.

We claim:

1. A stabilized chlorinated solvent composition consisting essentially of perchloroethylene or trichloroethylene and a stabilizer combination of from about 0.01 to about 0.5% N-methyl pyrrole together with from about 0.1 to about 1% of ethyl acetate, acetonitrile or pyrazine, based on the total weight of solvent and stabilizer combination.

2. The composition of claim 1 wherein the stabilized chlorinated solvent is trichloroethylene.

3. The composition of claim 2 wherein the stabilizer combination contains ethyl acetate.

4. The composition of claim 2 wherein the stabilizer combination contains acetonitrile.

5. The composition of claim 2 wherein the stabilizer combination contains pyrazine.

6. The composition of claims 3, 4 or 5 wherein the stabilizer contains the preferred amount of N-methyl pyrrole of from about 0.02 to about 0.05%.

* * * * *